United States Patent [19]

Hirose et al.

[11] Patent Number: 5,391,797
[45] Date of Patent: Feb. 21, 1995

[54] PROCESS FOR PREPARING ALKOXYSILANE

[75] Inventors: Toshifumi Hirose; Katsuya Ouchi, both of Kobe; Hiroshi Awaji, Akashi, all of Japan

[73] Assignee: Kanegafuchi Chemical Industry Co., Ltd., Osaka, Japan

[21] Appl. No.: 220,594

[22] Filed: Mar. 31, 1994

[30] Foreign Application Priority Data

Apr. 2, 1993 [JP] Japan .................. 5-098408
Sep. 30, 1993 [JP] Japan .................. 5-265480

[51] Int. Cl.⁶ ...................... C07F 7/08; C07F 7/18
[52] U.S. Cl. ........................................ 556/467
[58] Field of Search ............................. 556/467

[56] References Cited

U.S. PATENT DOCUMENTS

| | | |
|---|---|---|
| 2,626,273 | 1/1953 | Hunter et al. |
| 5,183,914 | 2/1993 | Yeh et al. ............. 556/467 |
| 5,258,537 | 11/1993 | Takeuchi et al. ........ 556/467 |
| 5,310,844 | 5/1994 | Weber et al. .......... 556/467 X |

OTHER PUBLICATIONS

M. Zenbayashi et al., "Preparation of Alkoxysilanes as Intermediates for Silicones", Chemical Abstracts, vol. 111, No. 15, Oct. 9, 1989 Abstract No. 134473a.
S. Soya et al., "Preparation of Trialkoxysilanes", Chemical Abstracts, vol. 112, No. 15, Apr. 9, 1990, Abstract No. 138595.

*Primary Examiner*—Paul F. Shaver
*Attorney, Agent, or Firm*—Foley & Lardner

[57] ABSTRACT

A process for preparing an alkoxysilane of the general formula:

$$R^3{}_b SiH_c(OR^2)_{4-(b+c)}$$

in which $R^2$ represents a substituted or unsubstituted alkyl group, $R^3$ represents a monovalent substituted or unsubstituted hydrocarbon group, b is 1, 2 or 3, and c is 0, 1, or 2, having the step of:
reacting an alkoxysilane of the general formula:

$$R^1{}_a Si(OR^2)_{4-a}$$

wherein $R^1$ represents a monovalent substituted or unsubstituted hydrocarbon group, $R^2$ is the same as defined above, and a is 0, 1, 2 or 3, with a polysiloxane in the presence of a catalyst containing an aluminum alkoxide, a zirconium alkoxide or a zirconium chelate to obtain the alkoxysilane, which process suppresses side reactions to provide the intended compound which is free from halogen compounds in a high yield.

9 Claims, No Drawings

PROCESS FOR PREPARING ALKOXYSILANE

FIELD OF THE INVENTION

The present invention relates to a process for preparing an alkoxysilane which is one of important intermediates in the field of silicone industry. More particularly, the present invention relates to a process for preparing an alkoxysilane in a high yield by a halogen-free process.

DESCRIPTION OF THE PRIOR ART

Japanese Patent Kokai No. 132590/1989 discloses a process for preparing an alkoxysilane, comprising the step of:

reacting an alkoxysilane of the general formula:

$$R^1{}_a Si(OR^2)_{4-a}$$

wherein $R^1$ represents a monovalent substituted or unsubstituted hydrocarbon group, $R^2$ represents an alkyl group, and a is 0, 1, 2 or 3, with a polysiloxane in the presence of a titanium compound catalyst to form an alkoxysilane of the general formula:

$$R^3{}_b SiH_c(OR^2)_{4-(b+c)}$$

wherein $R^2$ is the same as defined above, $R^3$ represents a monovalent substituted or unsubstituted hydrocarbon group, b is 1, 2 or 3, and c is 0, 1, or 2.

According to the above process, for example, tetramethoxysilane is reacted with polymethylhydrogensiloxane represented by the formula:

$$Me_3SiO—(MeHSiO)_{40}—SiOMe_3$$

to obtain dimethoxymethylsilane. Tetraethoxysilane is reacted with octamethylcyclotetrasiloxane represented by the formula:

$$(Me_2SiO)_4$$

to obtain diethoxydimethylsilane. In this process, the Si—O bonds in the polysiloxane molecule are said to be cleaved by the titanium compound used as a catalyst, followed by the insertion reaction of the alkoxy group from the alkoxysilane of the raw material into the cleaved portion to form the intended alkoxysilane.

The process has an advantage that halogen compounds such as hydrogen chloride and chlorosilane are not by-produced since the reaction is a halogen-free reaction. However, it has problems that many by-products other than the halogen compounds are formed in a large amount to lower the yield of the intended compound, requiring tedious purification procedure.

SUMMARY OF THE INVENTION

It is an object of the present invention to solve such problems and provide a process for preparing an alkoxysilane in a high purity and a high yield.

It has been found that, when an alkoxysilane is reacted with a polysiloxane in the presence of a catalyst comprising an aluminum alkoxide, a zirconium alkoxide or a zirconium chelate, byproducts are formed in a small amount in comparison with conventional methods to obtain the intended alkoxysilane in a high yield, thus making it easy to separate the byproducts from the desired alkoxysilane.

Accordingly, the present invention provides a process for preparing an alkoxysilane of the general formula:

$$R^3{}_b SiH_c(OR^2)_{4-(b+c)} \qquad (I)$$

wherein $R^2$ represents a substituted or unsubstituted alkyl group, $R^3$ represents a monovalent substituted or unsubstituted hydrocarbon group, b is 1, 2 or 3, and c is 0, 1, or 2, comprising the step of:

reacting an alkoxysilane of the general formula:

$$R^1{}_a Si(OR^2)_{4-a} \qquad (II)$$

wherein $R^1$ represents a monovalent substituted or unsubstituted hydrocarbon group, $R^2$ is the same as defined above, and a is 0, 1, 2 or 3, with a polysiloxane containing monovalent substituted or unsubstituted hydrocarbon groups in the presence of at least one catalyst selected from the group consisting of aluminum alkoxides, zirconium alkoxides and zirconium chelates to form the alkoxysilane.

DETAILED DESCRIPTION OF THE INVENTION

In the alkoxysilane of the general formula (II) which is used as a starting material, the alkoxy groups represented by $R^2O$ include methoxy, ethoxy, propoxy, butoxy group, etc. Methoxy and ethoxy groups are preferred since they have high reactivity. The number of the alkoxy group (4−a) may be from 1 to 4, being preferably 3 or 4 since high activity can be obtained.

The monovalent substituted or unsubstituted groups represented by $R^1$ in the general formula (II) include alkyl groups such as methyl, ethyl, propyl and butyl group, substituted alkyl groups such as chloromethyl group, alkenyl groups such as vinyl and allyl group, aryl groups such as phenyl and tolyl group, and aralkyl groups such as benzyl group. Examples of preferred alkoxysilanes used as a raw material are methyltrimethoxysilane, ethyltrimethoxysilane, methyltriethoxysilane, tetramethoxysilane, tetraethoxysilane, etc. Methyltrimethoxysilane, methyltriethoxysilane, tetramethoxysilane, and tetraethoxysilan are particularly preferred.

The alkoxysilanes obtained by the process according to the present invention include those having Si—H bonds in the molecule such as dimethylmethoxysilane, dimethylethoxysilane, methyldimethoxysilane, methyldiethoxysilane, methylvinylmethoxysilane, methylphenylmethoxysilane, etc., and those having no Si—H bonds in the molecule such as, dimethyldimethoxysilane, dimethyldiethoxysilane, dimethyldipropoxysilane, etc.

When the intended alkoxysilane has Si—H bonds in the molecule, the polysiloxanes having Si—H bonds are used as a raw materials. The polysiloxane used as a raw material may be any of linear, branched or cyclic polysiloxanes, or a mixture thereof. In such polysiloxanes, organic groups other than hydrogen atom which is bonded to the silicone atom may be alkyl groups such as methyl, ethyl, propyl and butyl group, substituted alkyl groups such as chloromethyl groups, alkenyl groups such as vinyl and allyl group, aryl groups such as phenyl and tolyl group and aralkyl groups such as benzyl group. Methyl group and ethyl group are preferred because of low cost. The polysiloxanes include linear polyhydrogensiloxanes of the formula:

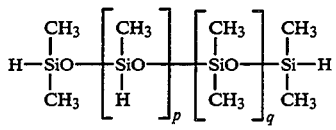

in which p is an integer of from 0 to 100 and q is an integer of 0 to 100, a linear polyhydrogensiloxane of the general formula:

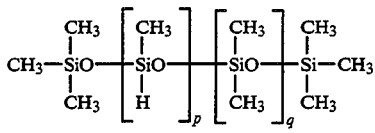

in which p is an integer of from 1 to 100 and q is an integer of from 0 to 100.

a cyclic polyhydrogensiloxane of the general formula:

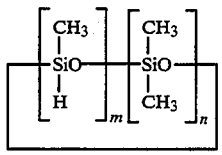

wherein m is an integer of from 1 to 6 and n is an integer of from 0 to 5, etc.

The content of the Si—H bonds in the polysiloxane is not particularly limited. However, when the preparation of the alkoxysilane having Si—H bonds in the molecule is intended, the polysiloxane having a higher content of the bonds is preferred since it provides the alkoxysilane in a higher yield. More specifically, examples of the polysiloxanes described above are a compound of the formula:

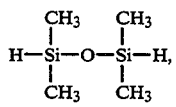

a compound of the formula:

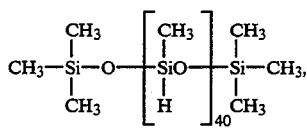

a branched polymethylhydrogensiloxane comprising $(CH_3)_2HSiO_{0.5}$ and $SiO_2$ units of which the hydrogen content is 1.03% by weight, and which has a viscosity of 24 cSt at a temperature of 25° C., and a polysiloxane of the general formula:

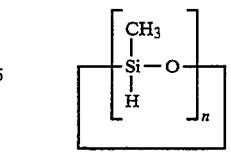

wherein n is an integer of from 3 to 8. Polymethylhydrogensiloxane is preferred from the points of view of yield and cost.

When the intended alkoxysilane has no Si—H bond in the molecule, the polysiloxane having no Si—H bond in the molecule is used as a raw material. In such polysiloxanes, organic groups other than hydrogen atoms attached to the silicone atom include monovalent hydrocarbon groups such as alkyl groups, alkenyl groups, e.g. vinyl or ally group, and aryl groups, e.g. phenyl group and tolyl group, and aralkyl groups, e.g. benzyl group. The monovalent hydrocarbon groups may be substituted hydrocarbon groups, for example, halogen substituted hydrocarbon groups such as chloromethyl group. The carbon atom number of the monovalent hydrocarbon group may be not more than 10, preferably not more than 8. Methyl and ethyl groups are particularly preferred in view of cost.

The molar ratio of the alkoxysilane used as the raw material to the polysiloxane is not critical. However, it is usually selected in such a proportion that the ratio of the Si content in the alkoxysilane to the content in the polysiloxane is in the range of 0.1 to 10 in mole, preferably in the range of 0.2 to 5.

Aluminum alkoxides used as a catalyst in the process according to the present invention are represented by the general formula:

$$(R^2O)_d AlX_{3-d}$$

wherein $R^2$ represents an unsubstituted or substituted alkyl group, X represents a monovalent anionic group other than an alkoxy group, d is 1, 2, or 3. The most preferred aluminum alkoxide is aluminum trialkoxide of the formula $(R^2O)_3Al$, in which a portion of $R^2O$ may, however, be substituted by X, etc. Preferred X is an anionic group represented by the general formula:

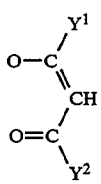

wherein $Y^1$ and $Y^2$ independently represent an alkyl or alkoxy group containing carbon atoms of from 1 to 8.

Specific examples of the aluminum alkoxides are aluminum triisopropoxide, aluminum tri-sec-butoxide, aluminum diisopropoxy-sec-butoxide, aluminum diisopropoxide acetylacetonate, aluminum sec-butoxide acetylacetonate, aluminum diisopropoxide ethylacetoacetate, aluminum di-sec-butoxide ethylacetoacetate. Those aluminum alkoxides may be used as such or in the form of a solution in appropriate solvents such as alcohol.

Zirconium alkoxides or chelates used as a catalyst in the present invention are represented by the general formula:

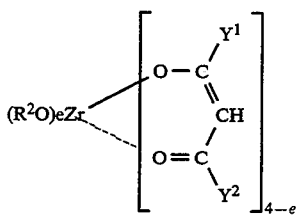

wherein $R^2$ is the same as defined above, $Y^1$ and $Y^2$ independently represent an alkyl or alkoxy group having carbon atoms of from 1 to 8, and e is 0, 1, 2, 3 or 4. The most preferred zirconium alkoxide or chelate is zirconium tetraalkoxide of the formula of $(R^2O)_4Zr$, in which $R^2O$ may, however, be partially or wholly substituted by the group of the general formula:

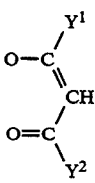

wherein $Y^1$ and $Y^2$ are the same as defined above.

Specific examples of the zirconium alkoxides or chelates are zirconium tetrabutoxide, zirconium tetraisopropoxide, zirconium tetramethoxide, zirconium tributoxide monoacetylacetonate, zirconium dibutoxide bisacetylacetonate, zirconium monobutoxide trisacetylacetonate, zirconium tributoxide monoethylacetoacetate, zirconium dibutoxide bisethylacetoacetate, zirconium monobutoxide trisethylacetoacetate, zirconium tetraacetylacetonate, zirconium teraethylacetoacetate. Zirconium.-butoxide is particularly preferred among zirconium alkoxides.

Those zirconium alkoxides or chelates may be used as such or in the form of a solution in an appropriate solvent such as hydrocarbons.

The amount of the catalyst used in the process according to the present invention can be selected in a wide range depending on a desired reaction rate. It is generally in the range of from 0.1 to 10% by weight, preferably from 0.5 to 5% by weight, based on the starting materials.

The reaction is carried out at a temperature at which the desired reaction product can be easily distilled off. For this purpose, it is generally desirable to carry out the reaction under atmospheric pressure while low pressure or high pressure may be used. The reaction temperature is usually from about 60° to 300° C., preferably from 100° to 200° C.

The order of the addition of the reactants and the catalyst for the reaction is as follows: A portion of the alkoxysilane to be used and the aluminum alkoxide, or the zirconium alkoxide or chelate catalyst may be mixed and preheated. The mixture of the remaining alkoxysilane and the polysiloxane may be then added dropwise thereto to effect the reaction. Alternatively, the whole of the alkoxysilane to be used and the aluminum alkoxide, or the zirconium alkoxide or chelate catalyst may be mixed and preheated. The polysiloxane may be then added dropwise thereto to effect the reaction. Alternatively, the alkoxysilane, the polysiloxane and the aluminum alkoxide, or the zirconium alkoxide or chelate catalyst may be mixed, followed by heating the mixture to effect the reaction. In all the cases, it is particularly desirable to rapidly distill off the reaction product to suppress side reactions.

The process according to the present invention may be carried out in the presence of a solvent. For example, an inert solvent having a higher boiling point than the intended alkoxysilane, e.g. toluene and xylene is preferably used.

According to the present invention, any halogen compound such as hydrogen chloride, chlorosilane, etc. is not by-produced, and the amount of undesired by-products other than the halogen compounds is also small, so that alkoxysilane containing no halogen compounds can be produced in a high yield and a high purity.

EXAMPLES

The present invention will be illustrated by Examples and Comparative Examples more specifically.

Example 1

Into a 300 ml four-necked flask equipped with a thermometer, a mechanical stirrer, a dropping funnel, a distillation tower which had a length of 30 cm and was packed with Rasich rings and a distillation head, there were charged 10.00 g (0.066 mole) of tetramethoxysilane (commercially available from Shinetsu Chemicals) and 0.46 g (0.0023 mole, 0.78% by weight of the total weight of the silane and the polysiloxane used) of aluminum triisopropoxide (commercially available from Nakarai Chemicals).

The content in the flask was heated to a temperature of 130° C. with stirring. Then the mixture of 31.04 g (0.204 mole) of tetramethoxysilane and 17.30 g (0.270 mole, converted to Si—H bonds) of polymethylhydrogensiloxane having the formula of $Me_3SiO$—$(MeHSiO)_{40}$—$SiMe_3$ (commercially available from Shinetsu Chemicals) was added dropwise thereto over about one hour. After the completion of dropwise addition, the content in the flask was continued to be stirred for 2 hours while increasing the temperature up to about 190° C.

During the period from the start of the dropwise addition to the completion of the heating with stirring, 24.00 g of distillate having a boiling range of from 40° to 62° C. was obtained.

Gas chromatography and $^1H$ NMR analyses showed that the distillate contained $Me(MeO)_2SiH$ of 99% and $Me(MeO)SiH_2$ of 1%. The yield, based on the Si—H groups in the raw polysiloxane, was 82% for $Me(MeO)_2SiH$ and 1% for $Me(MeO)SiH_2$. The alkali decomposition analysis of the residue in the flask showed the remaining Si—H groups of 5% in the residue, based on the Si—H groups in the raw polysiloxane.

Example 2

Using the similar apparatus to that in Example 1, 10.00 g (0.066 mole) of tetramethoxysilane (commercially available from Shinetsu Chemicals) and 0.55 g (0.0024 mole, 0.94% by weight of the total weight of the silane and the polysiloxane used) of aluminum tri-sec-butoxide (commercially available from Tokyo Chemicals) were charged into the flask.

The content in the flask was heated to a temperature of 130° C. with stirring. Then the mixture of 31.04 g (0.204 mole) of tetramethoxysilane and 17.30 g (0.270 mole, converted to Si—H bonds) of polymethylhydrogensiloxane having the formula of Me$_3$SiO—(MeHSiO)$_{40}$—SiMe$_3$ (commercially available from Shinetsu Chemicals) was added dropwise thereto over about one hour. After the completion of dropwise addition, the content in the flask was continued to be stirred for two hours while increasing the temperature up to about 190° C.

During the period from the start of the dropwise addition to the completion of the heating with stirring, 23.42 g of distillate having a boiling range of from 40° to 62° C. was obtained.

Gas chromatography and $^1$H NMR analyses showed that the distillate contained Me(MeO)$_2$SiH of 95% and Me(MeO)SiH$_2$ of 5%. The yield, based on the Si—H groups in the raw polysiloxane, was 75% for Me(MeO)$_2$SiH and 5% for Me(MeO)SiH$_2$. The alkali decomposition analysis of the residue in the flask showed the remaining Si—H groups of 7% in the residue, based on the Si—H groups in the raw polysiloxane.

Example 3

Using the similar apparatus to that in Example 1, 8.95 g (0.066 mole) of methyltrimethoxysilane (commercially available from Shinetsu Chemicals) and 0.46 g (0.0024 mole, 0.85% by weight of the total weight of the silane and the polysiloxane used) of aluminum triisopropoxide (commercially available from Nakarai Chemicals) were charged into a flask.

The content in the flask was heated to a temperature of 130° C. with stirring. Then the mixture of 27.70 g (0.204 mole) of methyltrimethoxysilane and 17.30 g (0.270 mole, converted to Si—H bonds) of polymethylhydrogensiloxane having the formula of Me$_3$SiO—(MeHSiO)$_{40}$—SiMe$_3$ (commercially available from Shinetsu Chemicals) was added dropwise thereto over about one hour. After the completion of dropwise addition, the contents in the flask were continued to be stirred for two hours while increasing the temperature up to about 190° C.

During the period from the start of the dropwise addition to the completion of the heating with stirring, 21.35 g of distillate having a boiling range of from 40° to 62° C. was obtained.

Gas chromatography and $^1$H NMR analyses showed that the distillate contained Me(MeO)$_2$SiH of 95% and Me(MeO)SiH$_2$ of 5%. The yield, based on the Si—H group in the raw polysiloxane, was 71% for Me(MeO)$_2$SiH and 5% for Me(MeO)SiH$_2$. The alkali decomposition analysis of the residue in the flask showed the remaining Si—H groups of 3% in the residue, based on the Si—H groups in the raw polysiloxane.

Example 4

Using the similar apparatus to that in Example 1, 10.00 g (0.066 mole) of tetramethoxysilane (commercially available from Shinetsu Chemicals) and 0.86 g (0.0023 mole) of zirconium tetrabutoxide (commercially available from Matsumoto Pharmacy) were charged into a flask.

The content in the flask was heated to a temperature of 117° C. with stirring. Then the mixture of 31.04 g (0.204 mole) of tetramethoxysilane and 17.30 g (0.270 mole, converted to Si—H bonds) of polymethylhydrogensiloxane having the formula of Me$_3$SiO—(MeHSiO)$_{40}$—SiOMe$_3$ commercially available from Shinetsu Chemicals) was added dropwise thereto over about one hour. After the completion of dropwise addition, the contents in the flask were continued to be stirred for 2 hours while increasing the temperature up to about 180° C.

During the period from the start of the dropwise addition to the completion of the heating with stirring, 23.37 g of distillate having a boiling range of from 40° to 62° C. was obtained.

The gas chromatography and $^1$H NMR analyses of the distillate and the residue in the flask showed that the yield, based on the Si—H group in the raw polysiloxane, was 74% for Me(MeO)$_2$SiH, 2% for Me(MeO)SiH$_2$, 3% for (MeO)$_3$SiH, 4% for MeSi(OMe)$_3$ and 0% for the unreacted Si(OMe)$_4$. The alkali decomposition analysis of the residue showed the remaining Si—H group of 4% in the residue (based on the Si—H groups in the raw polysiloxane).

Example 5

Using the similar apparatus to that in Example 1, 15.00 g (0.099 mole) of tetramethoxysilane (commercially available from Shinetsu Chemicals) and 0.86 g (0.0023 mole) of zirconium tetrabutoxide (commercially available from Matsumoto Pharmacy) were charged into a flask.

The content in the flask was heated to a temperature of 117° C. with stirring. Then the mixture of 46.6 g (0.306 mole) of tetramethoxysilane and 17.30 g (0.270 mole, converted to Si—H bonds) of polymethylhydrogensiloxane having the formula of Me$_3$SiO—(MeHSiO)$_{40}$—SiOMe$_3$ (commercially available from Shinetsu Chemicals) was added dropwise thereto over about one hour. After the completion of dropwise addition, the content in the flask was continued to be stirred for 2 hours while increasing the temperature up to about 180° C.

During the period from the start of the dropwise addition to the completion of the heating with stirring, 32.11 g of distillate having a boiling range of from 40° to 62° C. was obtained.

The gas chromatography and $^1$H NMR analyses of the distillate and the residue in the flask showed that the yield, based on the Si—H group in the raw polysiloxane, was 81% for Me(MeO)$_2$SiH, 2% for Me(MeO)SiH$_2$, 5% for (MeO)$_3$SiH, 4% for MeSi(OMe)$_3$ and 42% for the unreacted Si(OMe)$_4$. The alkali decomposition analysis of the residue showed the remaining Si—H group of 4% in the residue (based on the Si—H groups in the raw polysiloxane).

Example 6

Using the similar apparatus to that in Example 1, 8.95 g (0.066 mole) of methyltrimethoxysilane (commercially available from Shinetsu Chemicals) and 0.98 g (0.0023 mole) of zirconium dibutoxybisacetylacetonate were charged into a flask.

The content in the flask was heated to a temperature of 100° C. with stirring. Then the mixture of 27.70 g (0.204 mole) of methyltrimethoxysilane and 17.30 g (0.270 mole, converted to Si—H bonds) of polymethylhydrogensiloxane having the formula of Me$_3$SiO—(MeHSiO)$_{40}$—SiOMe$_3$ (commercially available from Shinetsu Chemicals) was added dropwise thereto over about one hour. After the completion of dropwise addition, the content in the flask was continued to be stirred for 2 hours while increasing the temperature up to about 180° C.

During the period from the start of the dropwise addition to the completion of the heating with stirring, 23.41 g of distillate having a boiling range of from 40° to 62° C. was obtained.

The gas chromatography and $^1$H NMR analyses of the distillate and the residue in the flask showed that the yield, based on the Si—H groups in the raw polysiloxane, was 77% for Me(MeO)$_2$SiH, 3% for Me(MeO)SiH$_2$, 3% for (MeO)$_3$SiH, and 4% for the unreacted MeSi(OMe)$_3$. The alkali decomposition analysis of the residue showed no remaining Si—H groups in the residue (based on the Si—H groups in the raw polysiloxane).

Example 7

Using the similar apparatus to that in Example 1, 13.4 g (0.099 mole) of methyltrimethoxysilane (commercially available from Shinetsu Chemicals) and 0.98 g (0.0023 mole) of zirconium dibutoxide bisacetylacetonate were charged into a flask.

The content in the flask was heated to a temperature of 100° C. with stirring. Then the mixture of 41.62 g (0.306 mole) of methyltrimethoxysilane and 17.30 g (0.270 mole, converted to Si—H bonds) of polymethylhydrogensiloxane having the formula of Me$_3$SiO—(MeHSiO)$_{40}$—SiOMe$_3$ (commercially available from Shinetsu Chemicals) was added dropwise thereto over about one hour. After the completion of dropwise addition, the content in the flask was continued to be stirred for 2 hours while increasing the temperature up to about 180° C.

During the period from the start of the dropwise addition to the completion of the heating with stirring, 41.03 g of distillate having a boiling range of from 40° to 62° C. was obtained.

The gas chromatography and $^1$H NMR analyses of the distillate and the residue in the flask showed that the yield, based on the Si—H groups in the raw polysiloxane, was 86% for Me(MeO)$_2$SiH, 3% for Me(MeO)SiH$_2$, 4% for (MeO)$_3$SiH, and 46% for the unreacted MeSi(OMe)$_3$. The alkali decomposition analysis of the residue showed the remaining Si—H groups of 1% in the residue (based on the Si—H groups in the raw polysiloxane).

Comparative Example 1

Using the similar apparatus to that in Example 1, 10.00 g (0.066 mole) of tetramethoxysilane (commercially available from Shinetsu Chemicals) and 0.23 g (0.00068 mole) of titanium tetrabutoxide monomer were charged in to a flask.

The content in the flask was heated to a temperature of 110° C. with stirring. Then the mixture of 31.04 g (0.204 mole) of tetramethoxysilane and 17.30 g (0.270 mole, converted to Si—H bonds) of polymethylhydrogensiloxane having the formula of Me$_3$SiO—(MeHSiO)$_{40}$—SiMe$_3$ (commercially available from Shinetsu Chemicals) was added dropwise thereto over about one hour. After the completion of dropwise addition, the content in the flask was continued to be stirred for 2 hours while increasing the temperature up to about 170° C.

During the period from the start of the dropwise addition to the completion of the heating with stirring, 22.43 g of distillate having a boiling range of from 40° to 62° C.

The gas chromatography and $^1$H NMR analyses of the distillate and the residue in the flask showed that the yield, based on the Si—H groups in the raw polysiloxane, was 68% for Me(MeO)$_2$SiH, 5% for Me(MeO)SiH$_2$, 3% for (MeO)$_3$SiH, and 1% for MeSi(OMe)$_3$. The alkali decomposition analysis of the residue showed the remaining Si—H groups of 8% in the residue (based on the Si—H groups in the raw polysiloxane).

Comparative Example 2

Using the similar apparatus to that in Example, 1, 8.95 g (0.066 mole) of methyltrimethoxysilane (commercially available from Shinetsu Chemicals) and 0.23 g (0.00068 mole) of titanium tetrabutoxide monomer (commercially available from Wako Chemicals) were charged into a flask.

The content in the flask was heated to a temperature of 110° C. with stirring. Then the mixture of 27.70 g (0.204 mole) of methyltrimethoxysilane and 17.30 g (0.270 mole, converted to Si—H bonds) of polymethylhydrogensiloxane having the formula of Me$_3$SiO—(MeHSiO)$_{40}$—SiOMe$_3$ (commercially available from Shinetsu Chemicals) was added dropwise thereto over about one hour. After the completion of dropwise addition, the content in the flask was continued to be stirred for 2 hours while increasing the temperature up to about 190° C.

During the period from the start of the dropwise addition to the completion of the heating with stirring, 30.84 g of distillate having a boiling range of from 40° to 62° C. was obtained.

The gas chromatography and $^1$H NMR analyses of the distillate and the residue in the flask showed that the yield, based on the Si—H group in the raw polysiloxane, was 68% for Me(MeO)$_2$SiH, 17% for Me(MeO)SiH$_2$, 0% for (MeO)$_3$SiH, and 26% for the unreacted MeSi(OMe)$_3$. The alkali decomposition analysis of the residue showed the remaining Si—H groups of 0% in the residue (based on the Si—H groups in the raw polysiloxane).

The reaction condition, the Me(MeO)$_2$SiH content in the distillate, the yields of Me(MeO)$_2$SiH, Me(MeO)SiH$_2$, (MeO)$_3$SiH, MeSi(OMe)$_3$ and Si(OMe)$_4$, and the remaining Si—H groups in the residue were summarized in Tables 1 and 2.

TABLE 1

|  | Example | | | Comp. Example | |
| --- | --- | --- | --- | --- | --- |
|  | 1 | 2 | 3 | 1 | 2 |
| Reaction Condition: | | | | | |
| Catalyst | Al(O i-Pr)$_3$ | Al(O s-Bu)$_3$ | Al(O i-Pr)$_3$ | Ti(O n-Bu)$_4$ | Ti(O n-Bu)$_4$ |
| Alkoxisilane | Si(OMe)$_4$ | Si(OMe)$_4$ | MeSi(OMe)$_3$ | Si(OMe)$_4$ | MeSi(OMe)$_3$ |
| Molar Ratio of SiH/alkoxislane | 1/1 | 1/1 | 1/1 | 1/1 | 1/1 |
| Content of Me(MeO)$_2$SiH in Distillate: (%) | 99 | 95 | 95 | 87 | 63 |
| Yield: (%) | | | | | |
| Me(MeO)$_2$SiH | 82 | 75 | 71 | 68 | 68 |
| Me(MeO)SiH$_2$ | 2 | 5 | 5 | 5 | 17 |

TABLE 1-continued

|  | Example | | | Comp. Example | |
|---|---|---|---|---|---|
|  | 1 | 2 | 3 | 1 | 2 |
| (MeO)$_3$SiH | 0 | 0 | — | 3 | 0 |
| MeSi(OMe)$_3$ | 0 | 0 | — | 1 | 26 |
| SiH in Residue: (%) | 5 | 7 | 3 | 8 | 0 |

TABLE 2

|  | Example | | | |
|---|---|---|---|---|
|  | 4 | 5 | 6 | 7 |
| Reaction Condition: | | | | |
| Catalyst (a*) | Zr(OBu)$_4$ | Zr(OBu)$_4$ | Zr(OBu)$_2$Bis | Zr(OBu)$_2$Bis |
| Alkoxisilane | Si(OMe)$_4$ | Si(OMe)$_4$ | MeSi(OMe)$_3$ | MeSi(OMe)$_3$ |
| Mole Ratio of SiH/alkoxislane | 1/1 | 1/1.5 | 1/1 | 1/1.5 |
| Yield: (%) | | | | |
| Me(MeO)$_2$SiH | 74 | 81 | 77 | 86 |
| Me(MeO)SiH$_2$ | 2 | 2 | 3 | 3 |
| (MeO)$_3$SiH | 3 | 5 | 3 | 4 |
| MeSi(OMe)$_3$ | 4 | 4 | 4 | 46 |
| Si(OMe)$_4$ | 0 | 42 | 0 | 0 |
| SiH in Residue: (%) | 4 | 4 | 0 | 1 |

(a*) Zr(OBu)$_2$Bis: zirconium dibutoxide bisacetylacetonate

What is claimed is

1. A process for preparing an alkoxysilane of the general formula:

$$R^3{}_bSiH_c(OR^2)_{4-(b+c)}$$

wherein $R^2$ represents a substituted or unsubstituted alkyl group, $R^3$ represents a monovalent substituted or unsubstituted hydrocarbon group, b is 1, 2 or 3, and c is 0, 1, or 2, comprising the step of:

reacting an alkoxysilane of the general formula:

$$R^1{}_aSi(OR^2)_{4-a}$$

wherein $R^1$ represents a monovalent substituted or unsubstituted hydrocarbon group, $R^2$ is the same as defined above, and a is 0, 1, 2 or 3, with a polysiloxane containing monovalent substituted or unsubstituted hydrocarbon groups in the presence of at least one catalyst selected from the group consisting of aluminum alkoxides, or zirconium alkoxides and zirconium chelates to obtain the alkoxysilane.

2. A process as claimed in claim 1 wherein $R^1$ is an alkyl, alkenyl, aryl or aralkyl group.

3. A process as claimed in claim 1 wherein $R^2O$ is a methoxy, ethoxy, propoxy or butoxy group.

4. A process as claimed in claim 1 wherein the monovalent hydrocarbon groups contained in the polysiloxane are an alkyl, alkenyl, aryl or aralkyl groups.

5. A process as claimed in claim 1 wherein the polysiloxane has Si—H bonds in the molecule.

6. A process as claimed in claim 5 wherein the polysiloxane is polymethylhydrogensiloxane.

7. A process as claimed in claim 1 wherein $R^3$ is an alkyl, alkenyl, aryl, or aralkyl group.

8. A process as claimed in claim 1 wherein the aluminum alkoxide used as the catalyst is represented by the general formula:

$$(R^2O)_dAlX_{3-d}$$

wherein $R^2$ represents an unsubstituted or substituted alkyl group, X represents a monovalent anionic group other than alkoxy group, and d is 1, 2, or 3.

9. A process as claimed in claim 1 wherein the zirconium alkoxide or chelate used as the catalyst is represented by the general formula:

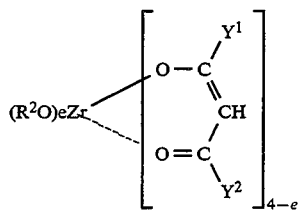

wherein $R^2$ is the same as defined above, $Y^1$ and $Y^2$ independently represent an alkyl or alkoxy group having carbon atoms of from 1 to 8, and e is 0, 1, 2, 3 or 4.

* * * * *